(12) United States Patent
Burkholz et al.

(10) Patent No.: US 11,547,832 B2
(45) Date of Patent: Jan. 10, 2023

(54) CATHETER DELIVERY DEVICE AND RELATED SYSTEMS AND METHODS

(71) Applicant: Becton, Dickinson and Company, Franklin Lakes, NJ (US)

(72) Inventors: Jonathan Karl Burkholz, Salt Lake City, UT (US); Jeffrey C. O'Bryan, Murray, UT (US); Daniel Blanchard, Bountiful, UT (US); Daniel Housley, Salt Lake City, UT (US); Marty Stout, South Jordan, UT (US); Eric Lindekugel, Salt Lake City, UT (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 163 days.

(21) Appl. No.: 16/742,013

(22) Filed: Jan. 14, 2020

(65) Prior Publication Data
US 2020/0230353 A1    Jul. 23, 2020

Related U.S. Application Data

(60) Provisional application No. 62/794,437, filed on Jan. 18, 2019.

(51) Int. Cl.
*A61M 25/00* (2006.01)
*A61M 39/10* (2006.01)
(Continued)

(52) U.S. Cl.
CPC .... *A61M 25/0026* (2013.01); *A61M 25/0105* (2013.01); *A61M 39/10* (2013.01); *G01N 33/49* (2013.01); *A61M 2039/1077* (2013.01)

(58) Field of Classification Search
CPC .. A61M 2025/0006; A61M 2025/0008; A61M 2025/0175; A61M 25/00; A61M 25/0026
See application file for complete search history.

(56) References Cited

U.S. PATENT DOCUMENTS

| 8,366,685 B2 | 2/2013 | Devgon |
| 9,186,100 B2 | 11/2015 | Devgon |
(Continued)

FOREIGN PATENT DOCUMENTS

| WO | 02/083228 | 10/2002 |
| WO | 2004/032995 | 4/2004 |
| WO | 2019/204413 | 10/2019 |

*Primary Examiner* — Deanna K Hall
(74) *Attorney, Agent, or Firm* — Kirton McConkie; Whitney Blair; Kevin Stinger

(57) ABSTRACT

A catheter system may include a catheter assembly and a catheter delivery device. The catheter assembly may include a catheter adapter, which may include a catheter adapter distal end, a catheter adapter proximal end, and a catheter adapter lumen extending through the catheter adapter distal end and the catheter adapter proximal end. The catheter assembly may include a primary catheter extending from the catheter adapter distal end. The catheter delivery device may include a housing, which may include a housing distal end coupled to the catheter assembly, a housing proximal end, and a housing lumen extending through the housing distal end and the housing proximal end. A secondary catheter may be disposed within the housing. The secondary catheter may be configured to move distally through the catheter assembly in response to a fluid pressure provided by a fluid delivery device coupled to the housing proximal end.

9 Claims, 12 Drawing Sheets

(51) Int. Cl.
*G01N 33/49* (2006.01)
*A61M 25/01* (2006.01)

(56) References Cited

U.S. PATENT DOCUMENTS

| | | |
|---|---|---|
| 9,839,385 B2 | 12/2017 | Burkholz |
| 9,925,356 B2 | 3/2018 | Reavill |
| 2008/0183141 A1* | 7/2008 | Reavill ............. A61M 25/0122 604/256 |
| 2012/0296314 A1 | 11/2012 | Reavill |
| 2014/0188002 A1 | 7/2014 | Close et al. |
| 2015/0005669 A1 | 1/2015 | Burkholz |
| 2017/0216564 A1* | 8/2017 | Devgon ........... A61B 5/150816 |
| 2018/0028800 A1* | 2/2018 | Devgon ............... A61B 8/0841 |

* cited by examiner

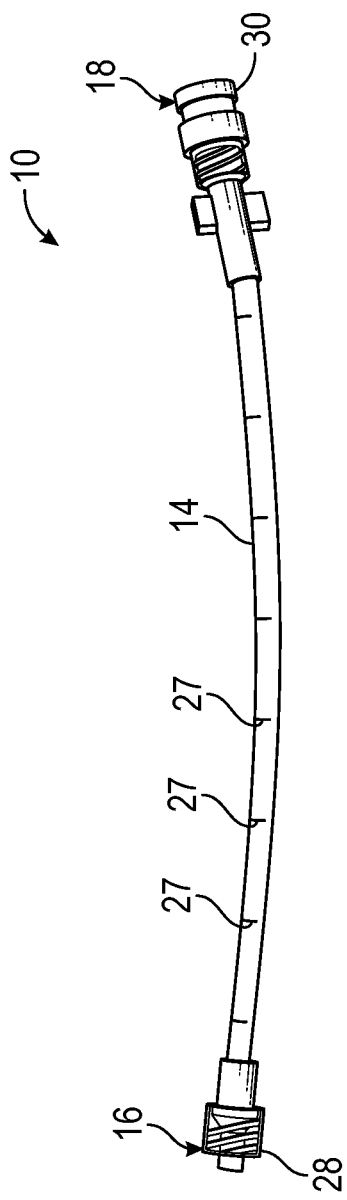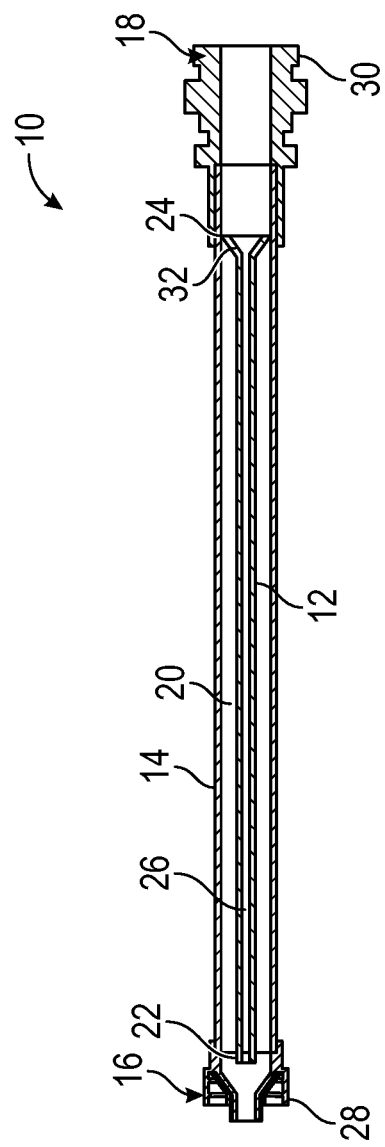
FIG. 1A
FIG. 1B

CATHETER DELIVERY DEVICE AND RELATED SYSTEMS AND METHODS

RELATED APPLICATIONS

This application claims the benefit of U.S. Provisional Patent Application No. 62/794,437, filed on Jan. 18, 2019, and entitled CATHETER DELIVERY DEVICE AND RELATED SYSTEMS AND METHODS, which is incorporated herein in its entirety.

BACKGROUND

Catheters are commonly used for a variety of infusion therapies. For example, catheters may be used for infusing fluids, such as normal saline solution, various medicaments, and total parenteral nutrition, into a patient. Catheters may also be used for withdrawing blood from the patient.

A common type of catheter is an over-the-needle peripheral intravenous ("IV") catheter. As its name implies, the over-the-needle catheter may be mounted over an introducer needle having a sharp distal tip. The catheter and the introducer needle may be assembled so that the distal tip of the introducer needle extends beyond the distal tip of the catheter with the bevel of the needle facing up away from skin of the patient. The catheter and introducer needle are generally inserted at a shallow angle through the skin into vasculature of the patient.

In order to verify proper placement of the introducer needle and/or the catheter in the blood vessel, a clinician generally confirms that there is "flashback" of blood in a flashback chamber of the catheter assembly. Once placement of the needle has been confirmed, the clinician may temporarily occlude flow in the vasculature and remove the needle, leaving the catheter in place for future blood withdrawal or fluid infusion.

Blood withdrawal using a peripheral IV catheter may be difficult for several reasons, particularly when an indwelling time of the catheter is more than one day. For example, when the catheter is left inserted in the patient for a prolonged period of time, the catheter or vein may be more susceptible to narrowing, collapse, kinking, blockage by debris (e.g., fibrin or platelet clots), and positioning of a tip of the catheter to the vasculature. Due to this, catheters may often be used for acquiring a blood sample at a time of catheter placement but are much less frequently used for acquiring a blood sample during the catheter indwell period. Therefore, when a blood sample is required, an additional needle stick is needed to provide vein access for blood collection, which may be painful for the patient and result in higher material costs. Accordingly, there is a need for catheter systems and methods that facilitate placement of blood sample instruments, such as, for example, catheters and probes, in the vasculature of the patient without additional needle sticks.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to a catheter delivery device to deliver a secondary catheter through a catheter assembly and into vasculature of a patient, as well as related systems and methods. In some embodiments, a catheter system may include the catheter delivery device and the catheter assembly. As used in the present disclosure, the term "distal" refers to a portion of the catheter system, or component thereof, that is farther from a clinician, and the term "proximal" refers to a portion of the catheter system, or component thereof, that is closer to the clinician.

In some embodiments, the catheter assembly may include a catheter adapter, which may include a catheter adapter distal end, a catheter adapter proximal end, and a catheter adapter lumen extending through the catheter adapter distal end and the catheter adapter proximal end. In some embodiments, the catheter assembly may include a primary catheter, which may be secured to the catheter adapter and may extend distally from the catheter adapter distal end. In some embodiments, the primary catheter may include a primary catheter distal end, a primary catheter proximal end, and a primary catheter lumen extending through the primary catheter distal end and the primary catheter proximal end.

In some embodiments, the catheter delivery device may include a housing, which may include a housing distal end, a housing proximal end, and a housing lumen extending through the housing distal end and the housing proximal end. In some embodiments, the housing distal end may be coupled to the catheter assembly. In some embodiments, the secondary catheter may be disposed within the housing. In some embodiments, the secondary catheter may include a secondary catheter distal end, a secondary catheter proximal end, and a secondary catheter lumen extending through the secondary catheter distal end and secondary catheter proximal end.

In some embodiments, the secondary catheter may be configured to move distally to an advanced position in response to a fluid pressure provided by a fluid delivery device. In some embodiments, the secondary catheter distal end may be disposed distal to the primary catheter distal end when the secondary catheter is in the advanced position.

In some embodiments, the housing distal end may include a distal connector and/or the housing proximal end may include a proximal connector. In some embodiments, the distal connector may include a male luer adapter or any other suitable connector. In some embodiments, the proximal connector may include a female luer adapter or any other suitable connector.

In some embodiments, the secondary catheter may include an expanded portion. In some embodiments, a diameter of the expanded portion may be greater than a diameter of a portion of the catheter system. In some embodiments, the portion of the catheter system may contact the expanded portion when the secondary catheter is disposed in the advanced position and may act as a stop to prevent distal movement of the secondary catheter. In some embodiments, the portion of the catheter system may be disposed in the housing lumen. For example, the portion of the catheter system may be disposed within the male luer adapter, which may be disposed at the housing distal end.

In some embodiments, the housing may include an extension tube, which may be flexible or semi-flexible. In some embodiments, a clamp may be disposed on the extension tube. In some embodiments, the clamp may be adjustable along the extension tube. In some embodiments, the clamp may decrease an inner diameter of the extension tube at a location of the clamp, creating the stop to prevent distal movement of the secondary catheter.

In some embodiments, the catheter system may include a first fluid pathway and a second fluid pathway. In some embodiments, within the catheter system, the first fluid pathway may be separate from and not in fluid communication with the second fluid pathway. In some embodiments, the catheter adapter may include a side port. In some embodiments, the first fluid pathway and/or the second fluid pathway may extend through the side port and the primary catheter. In some embodiments, the second fluid pathway may extend through the catheter adapter proximal end. In some embodiments, the second fluid pathway may extend through the secondary catheter, and the first fluid pathway may not extend through the secondary catheter.

In some embodiments, a first fluid may be delivered to the vasculature of the patient via the first fluid pathway, and a second fluid may be delivered to the vasculature of the patient via the second fluid pathway. In some embodiments, the first fluid may be delivered to the vasculature of the patient via the first fluid pathway at a same time as the second fluid is delivered to the vasculature of the patient via the second fluid pathway.

In some embodiments, a medicament may be delivered to the vasculature of the patient via the first fluid pathway and a flush or saline solution may be delivered to the vasculature of the patient via second fluid pathway. In some embodiments, the medicament may be delivered to the vasculature of the patient via the second fluid pathway and the flush or saline solution may be delivered to the vasculature of the patient via first fluid pathway. In these and other embodiments, extension of the secondary catheter beyond the primary catheter and further from an insertion site of the catheter assembly may facilitate delivery of the medicament to a healthier part of the vasculature with more blood flow, which may be particularly useful when the medicament is harsh.

In some embodiments, the primary catheter distal end may include a distal opening. In some embodiments, an outer circumference of the secondary catheter may be spaced apart from the distal opening such that fluid in the first fluid pathway may flow distally between the distal opening and the secondary catheter. In some embodiments, the secondary catheter distal end may include a slit configured to be closed under normal physiological conditions. In some embodiments, the secondary catheter distal end may include one or more diffuser holes.

In some embodiments, the distal opening of the primary catheter distal end may contact the outer circumference of the secondary catheter. In these and other embodiments, the primary catheter distal end may include a slit, which may be configured to be closed under normal physiological pressures. In some embodiments, the primary catheter distal end may include one or more diffuser holes.

In some embodiments, the secondary catheter may be constructed of a soft or flexible material. In some embodiments, the soft or flexible material and/or flushing during advancement of the secondary catheter may facilitate smooth placement of the secondary catheter within the vasculature of the patient, with little or no damage to the vasculature. In some embodiments, the flushing during the advancement of the secondary catheter may occur via the first fluid pathway and/or the second fluid pathway.

In some embodiments, the housing and/or other components of the catheter system may be transparent. In some embodiments, an outer surface of the secondary catheter may include one or more markings, which may indicate to a clinician a position of the secondary catheter distal end.

In some embodiments, a method of delivery of the secondary catheter to the catheter assembly, which may be indwelling and inserted within the vasculature of the patient, may include coupling the housing to the catheter assembly. In some embodiments, the method may include activating the fluid delivery device, which may be coupled to the housing. In some embodiments, in response to activating the fluid delivery device, fluid may flow distally through the housing and the catheter assembly. In some embodiments, the fluid may advance the secondary catheter through the catheter assembly in a distal direction. In some embodiments, activating the fluid delivery device may provide flushing of the catheter assembly and/or the vasculature as the secondary catheter advanced.

In some embodiments, the method may include priming the housing. In some embodiments, the housing may be primed prior to activation of the fluid delivery device. In some embodiments, the housing may be primed prior to coupling of the catheter delivery device to the catheter assembly. In some embodiments, the method may include uncoupling the fluid delivery device from the housing proximal end, and coupling a blood collection device to the housing proximal end.

In some embodiments, a blood sample may bay be collected within the blood collection device through the secondary catheter. In some embodiments, the method may include uncoupling the blood collection device from the housing proximal end and coupling another blood collection device to the housing proximal end. In some embodiments, another blood sample may be collected within the other blood collection device through the secondary catheter. Thus, in some embodiments, multiple blood samples may be collected from the patient without withdrawing the secondary catheter from the vasculature of the patient.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 1A is an upper perspective view of an example catheter delivery device, according to some embodiments;

FIG. 1B is a cross-sectional view of the catheter delivery device of FIG. 1A, according to some embodiments;

DESCRIPTION OF EMBODIMENTS

Figure 1C:
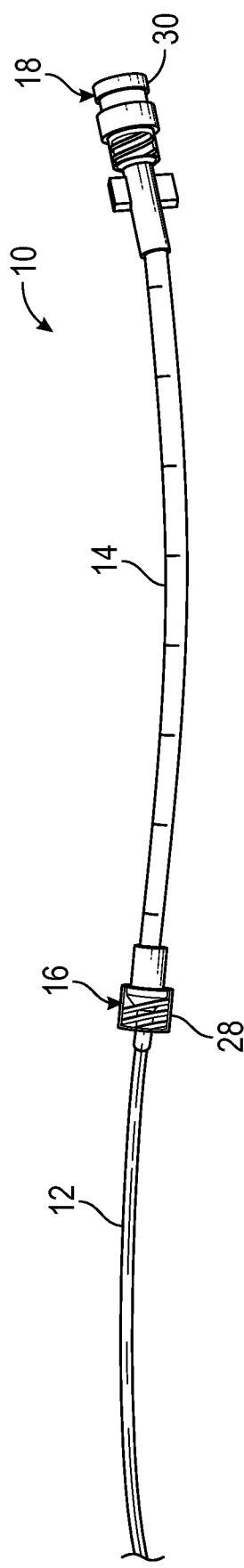
FIG. 1C is an upper perspective view of the catheter delivery device of FIG. 1A, illustrating an example secondary catheter in an example advanced position, according to some embodiments.

Referring now to FIG. 1A-1B, a catheter delivery device 10 may facilitate delivery of a secondary catheter 12 through a catheter assembly and into vasculature of a patient. In some embodiments, the catheter delivery device 10 may include a housing 14, which may include a housing distal end 16, which may be configured to couple to the catheter assembly. In some embodiments, the housing 14 may include a housing proximal end 18 and a housing lumen 20 extending through the housing distal end 16 and the housing proximal end 18.

In some embodiments, the secondary catheter 12 may be disposed within the housing 14. In some embodiments, the secondary catheter 12 may be loose or unattached within the housing lumen 20. In some embodiments, the secondary catheter 12 may include a secondary catheter distal end 22, a secondary catheter proximal end 24, and a secondary catheter lumen 26 extending through the secondary catheter distal end 22 and the secondary catheter proximal end 24.

In some embodiments, the secondary catheter 12 may be configured to move distally to an advanced position in response to a fluid pressure provided by a fluid delivery device, which may be coupled to the housing proximal end 18. In some embodiments, the housing 14 may be transparent. In some embodiments, an outer surface of the housing 14 may include one or more markings 27, which may indicate to the clinician a position of the secondary catheter distal end 22 within the catheter assembly or beyond a primary catheter of the catheter assembly.

FIGS. 1A-1B illustrate the secondary catheter 12 prior to activation of the fluid delivery device and distal movement of the secondary catheter 12 to the advanced position, according to some embodiments. In some embodiments, the housing lumen 20 may be smooth and may not include any catches for the secondary catheter 12 as it moves distally in response to activation of the fluid delivery device. In some embodiments, the housing lumen 20 may be non-tortuous.

In some embodiments, the secondary catheter 12 may provide structural support to the primary catheter of the indwelling catheter assembly. In some embodiments, the secondary catheter 12 may allow the user to draw a blood sample or infuse fluid through the secondary catheter 12 when the primary catheter is no longer functional or safe due to, for example, debris build up on a tip of the primary catheter and/or collapse of the primary catheter. Thus, in some embodiments, the secondary catheter 12 may reduce a number of needle sticks that the patient experiences as the primary catheter may be replaced less frequently. In some embodiments, the secondary catheter 12 may provide a second fluid pathway in addition to a first fluid pathway. In some embodiments, the first fluid pathway may be disposed between an outer surface of the secondary catheter 12 and an inner surface of the primary catheter, as will be described later in further detail.

In some embodiments, the secondary catheter 12 may be constructed of a soft or flexible material. In some embodiments, a material from which the secondary catheter 12 is constructed and/or flushing during advancement of the secondary catheter 12 may facilitate smooth placement of the secondary catheter 12 within the vasculature of the patient, with little or no damage to the vasculature. In some embodiments, the flushing during the advancement of the secondary catheter 12 may occur via the first fluid pathway and/or the second fluid pathway. In some embodiments, the secondary catheter 12 may be constructed of silicon, polyimide, latex, polyurethane, nylon, polyethylene, or another suitable material. In some embodiments, an outer surface of the secondary catheter 12 may include a lubricant, which may facilitate smooth advancement of the secondary catheter 12 in the distal direction.

In some embodiments, the housing distal end 16 may include a distal connector 28 and/or the housing proximal end 18 may include a proximal connector 30. In some embodiments, the distal connector 28 may include a slip or thread female luer adapter or a slip or thread male luer adapter or any other suitable connector. In some embodiments, the proximal connector 30 may include a slip or thread female luer adapter or a slip or thread male luer adapter or any other suitable connector including a needleless connector.

Figure 1D:
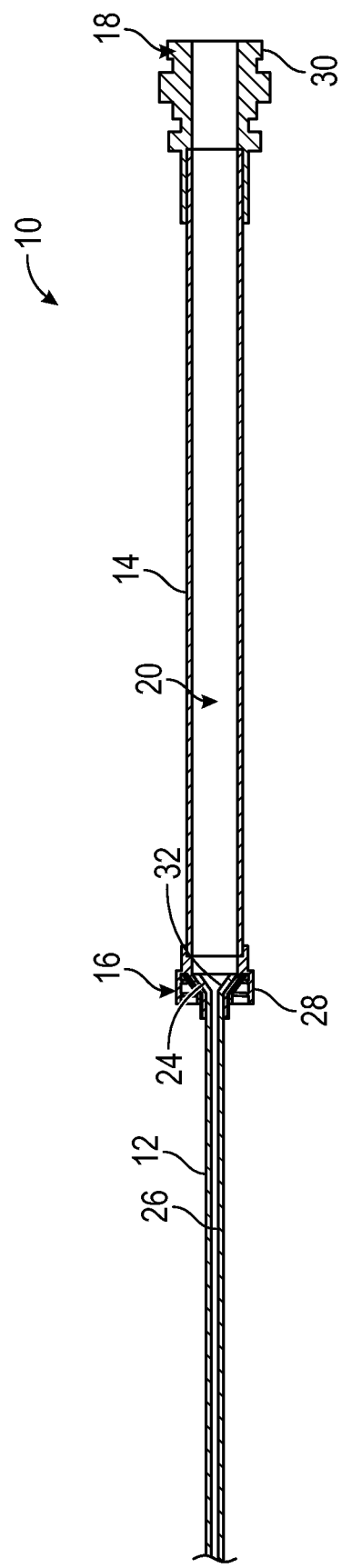
FIG. 1D is a cross-sectional view of the catheter delivery device of FIG. 1A, illustrating the secondary catheter in the advanced position, according to some embodiments.

In some embodiments, the secondary catheter 12 may include an expanded portion 32. In some embodiments, a diameter of the expanded portion 32 may be greater than a diameter of a portion of the housing lumen 20. In some embodiments, the expanded portion 32 may be tapered and may wedge against the portion of the housing lumen 20. Referring now to FIGS. 1C-1D, in some embodiments, the portion of the housing lumen 20 may contact the expanded portion 32 when the secondary catheter 12 is disposed in the advanced position and may act as a stop to prevent distal movement of the secondary catheter 12. In some embodiments, the portion of the housing lumen 20 may be disposed within a male luer adapter, which may be disposed at the housing distal end 16, as illustrated, for example, in FIG. 1D.

FIGS. 1C-1D illustrate the secondary catheter 12 in response to activation of the fluid delivery device, according to some embodiments. In some embodiments, in response to activation of the fluid delivery device, which may include a syringe or another fluid delivery device, fluid may be released from the fluid delivery device and may flow distally through the housing 14. In some embodiments, the fluid may cause distal movement of the secondary catheter 12 to the advanced position, according to some embodiments. In some embodiments, administration of a first amount of fluid via the fluid delivery device may partially advance the secondary catheter 12. In some embodiments, administration of an additional amount of fluid via the fluid delivery device may advance the secondary catheter 12 to the advanced position.

Figure 2A:
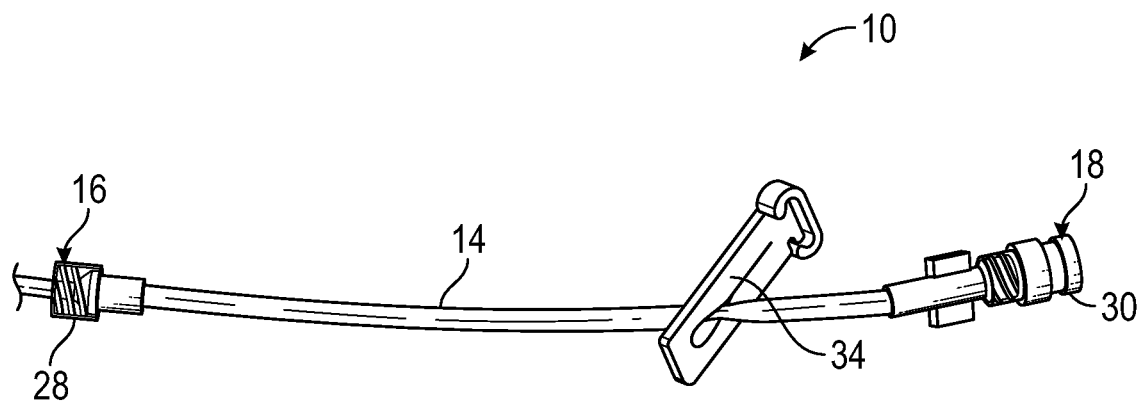
FIG. 2A is an upper perspective view of the catheter delivery device of FIG. 1A, illustrating the secondary catheter in another example advanced position and an example clamp, according to some embodiments.
Figure 2B:
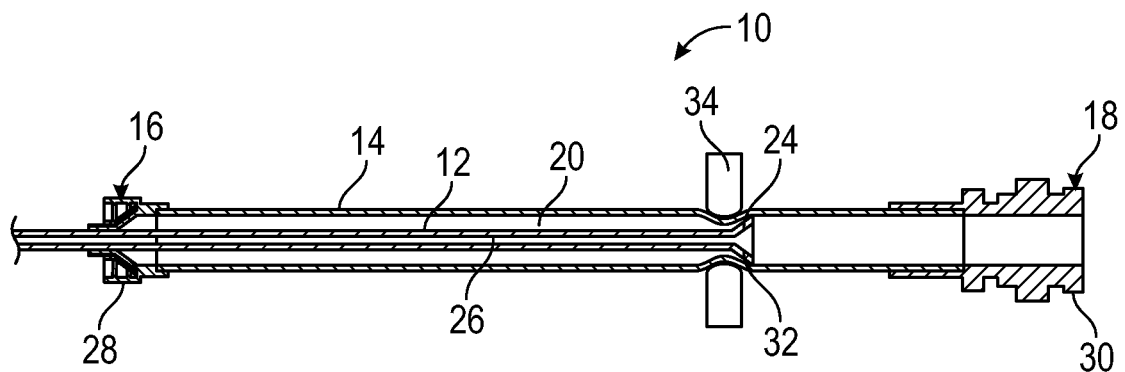
FIG. 2B is a cross-sectional view of the catheter delivery device of FIG. 1A, illustrating the secondary catheter in the other advanced position and the clamp of FIG. 2A, according to some embodiments.

Referring now to FIGS. 2A-2B, in some embodiments, the housing may include an extension tube, which may be flexible or semi-flexible. In some embodiments, a clamp 34 may be disposed on the extension tube. In some embodiments, the clamp 34 may be adjustable along the extension tube. In some embodiments, the clamp 34 may decrease an inner diameter of the extension tube at a location of the clamp 34, creating the stop to prevent distal movement of the secondary catheter 12.

Referring now to FIGS. 3A-3D, in some embodiments, a catheter system 36 may include the catheter delivery device 10 and the catheter assembly 38. In some embodiments, the catheter assembly 38 may include a catheter adapter 40, which may include a catheter adapter distal end 42, a catheter adapter proximal end 44, and a catheter adapter lumen 46 extending through the catheter adapter distal end 42 and the catheter adapter proximal end 44.

In some embodiments, the catheter assembly 38 may include the primary catheter 48, which may be secured to the catheter adapter 40 and may extend distally from the catheter adapter distal end 42. In some embodiments, the primary catheter 48 may include a primary catheter distal end 50, a primary catheter proximal end 52, and a primary catheter lumen 54 extending through the primary catheter distal end 50 and the primary catheter proximal end 52.

In some embodiments, the catheter system 36 may include a needle hub and an introducer needle extending distally from the needle hub through the primary catheter 48. In some embodiments, the needle hub and the introducer needle may be removed prior to movement of the secondary catheter 12 to the advanced position.

In some embodiments, the housing distal end 16 may be coupled to the catheter assembly 38 in various ways and configurations. In some embodiments, the housing distal end 16 may be coupled to the catheter assembly 38. In further detail, in some embodiments, the housing distal end 16 may be coupled to an extension set of the catheter assembly 38, which may extend from the catheter adapter 40. In some embodiments, the catheter system 36 may include one or more extension tubes, which may be arranged in various configurations. In some embodiments, the extension set may include an extension tube 53 and/or an extension tube 55. In some embodiments, the extension tube 53 may extend from the catheter adapter 40. In some embodiments, the extension set may include a connector 57, which may include a Y-connector or a T-connector. In some embodiments, the extension tube 55 may extend from a port of the connector 57. In some embodiments, the housing distal end 16 may be coupled to another port of the connector 57.

In some embodiments, a needleless connector 59 may be disposed at various locations within the catheter system 36. In some embodiments, the housing distal end 16 may be coupled to the needleless connector 59, which may be coupled to the catheter adapter 40 or the connector 57, for example. In some embodiments, a needleless connector 59 may be disposed at a proximal end of the extension set, as illustrated, for example, in FIGS. 3A-3D. In some embodiments, another fluid delivery device may be coupled to the needleless connector 59 or to the extension tube 55.

Figure 3A:
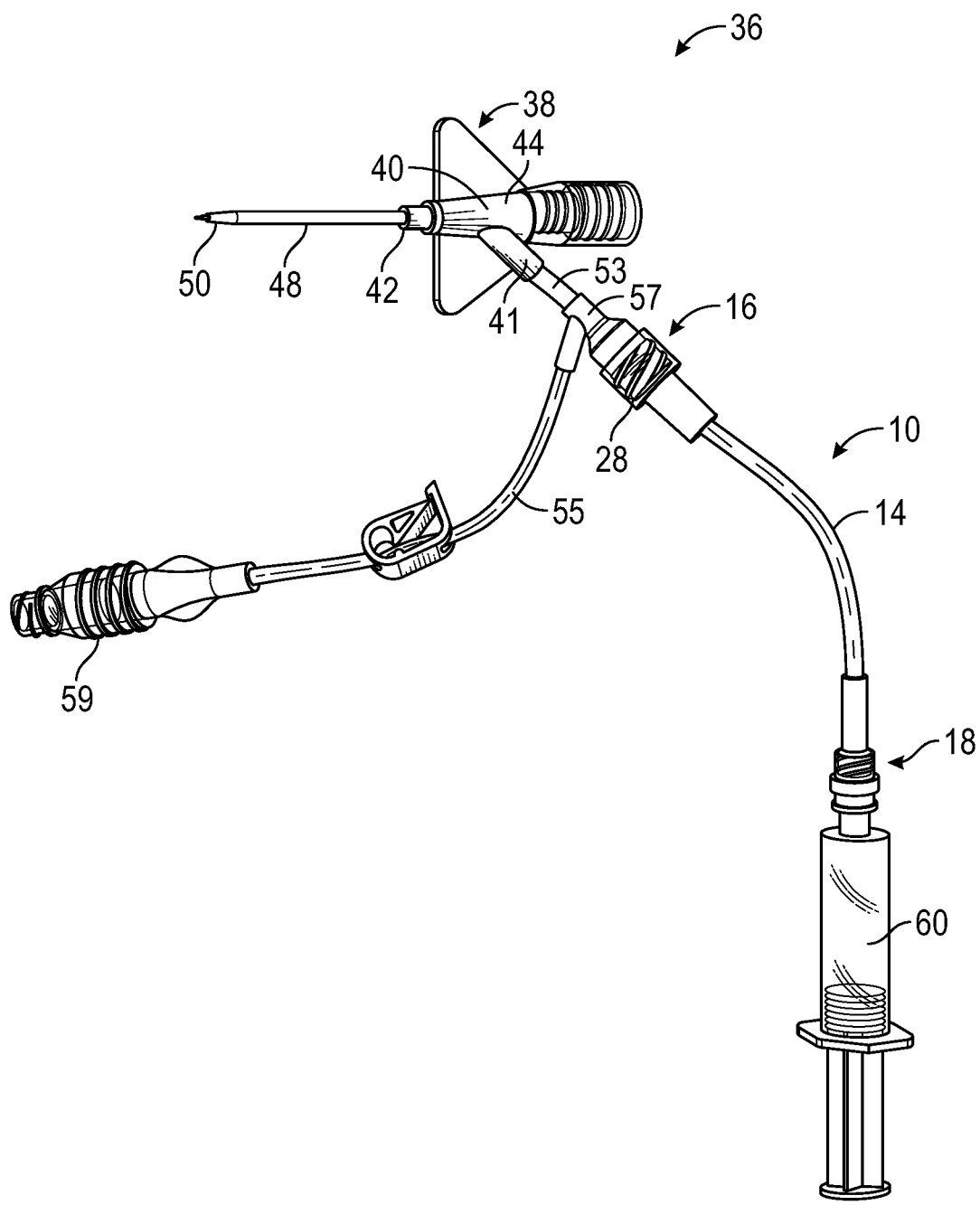
FIG. 3A is an upper perspective view of an example catheter system, illustrating the catheter delivery device of FIG. 1A coupled to an example catheter assembly, according to some embodiments.
Figure 3B:
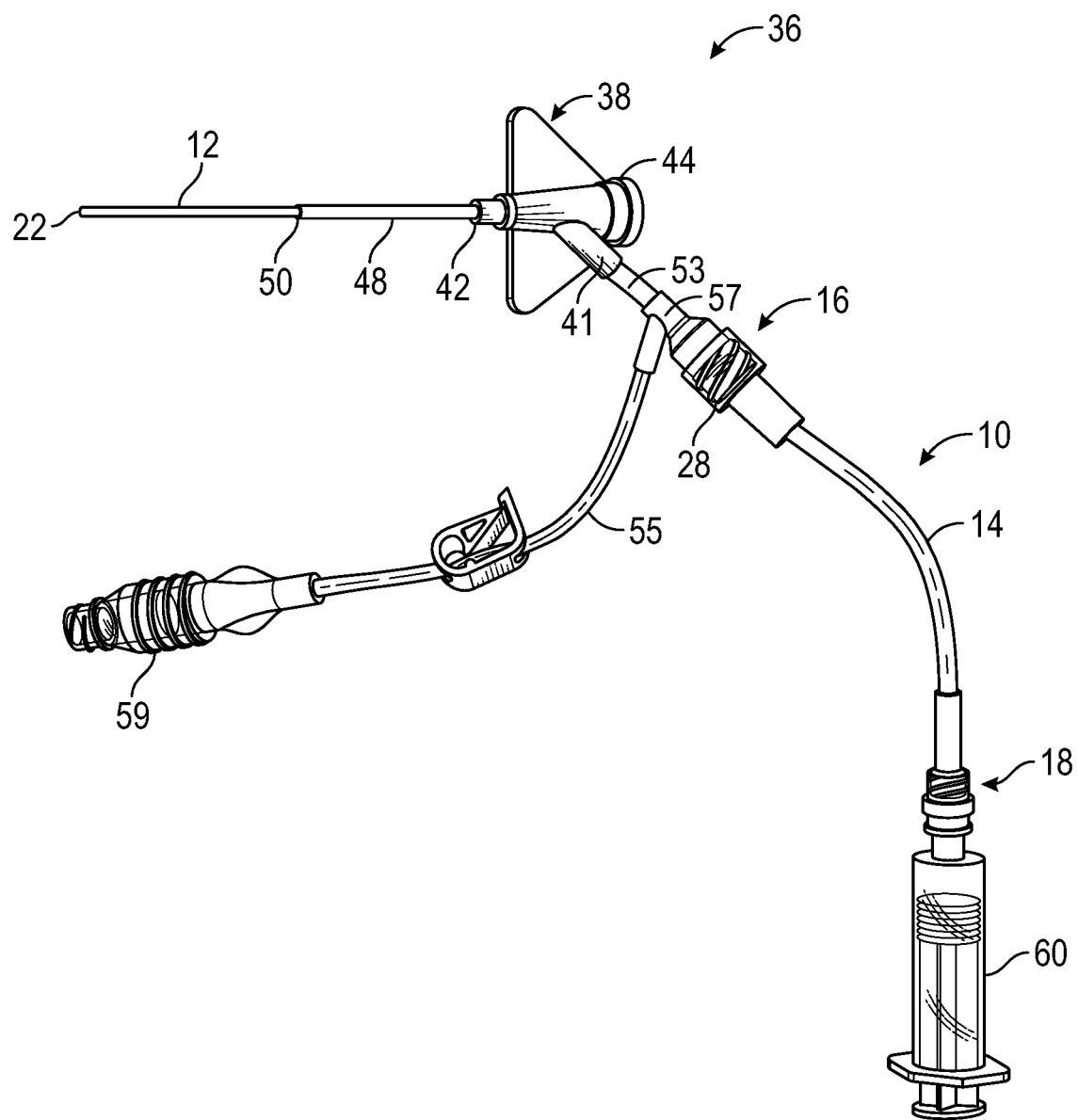
FIG. 3B is an upper perspective view of the catheter system of FIG. 3A, illustrating an example syringe after fluid infusion, according to some embodiments.
Figure 3C:
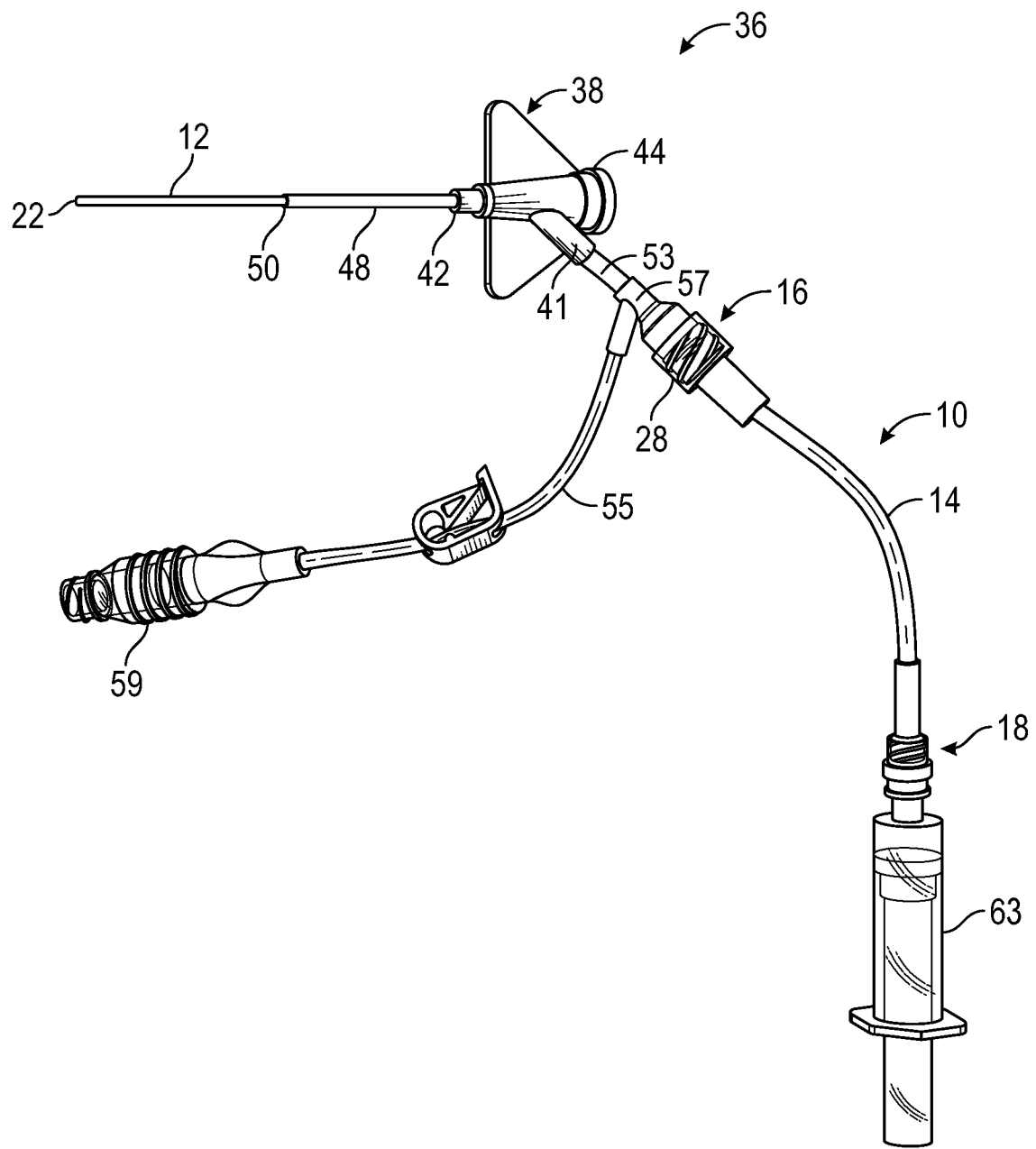
FIG. 3C is an upper perspective view of the catheter system of FIG. 3A, illustrating an example blood collection device coupled to the catheter delivery device, according to some embodiments.
Figure 3D:
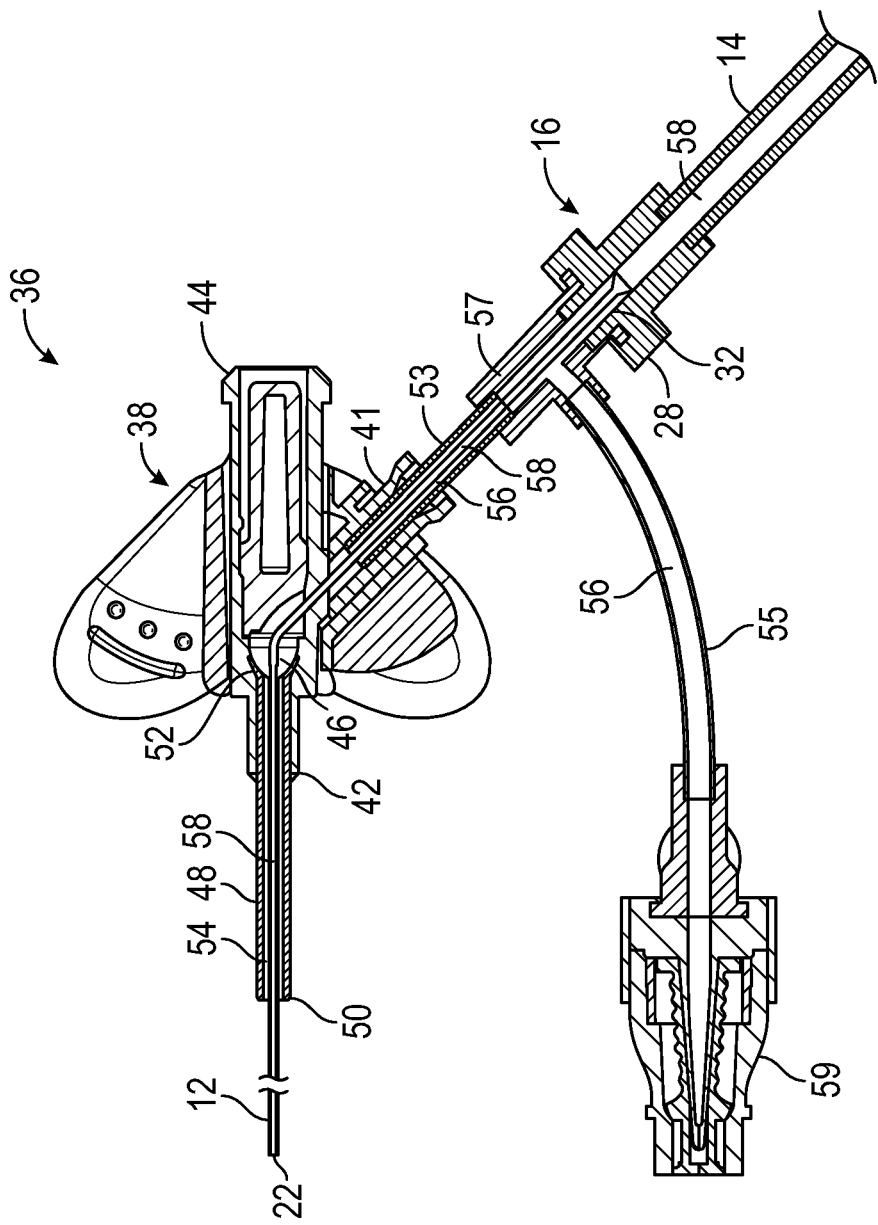
FIG. 3D is a cross-sectional view of the catheter system of FIG. 3A, according to some embodiments.

In some embodiments, the catheter system may include the first fluid pathway 56 and the second fluid pathway 58, as illustrated, for example, in FIG. 3D. In some embodiments, the other fluid delivery device may be configured to deliver fluid to the patient via the first fluid pathway 56. In some embodiments, the first fluid pathway 56 may be separate from and not in fluid communication with the second fluid pathway 58 within the catheter system. In some embodiments, the catheter adapter 40 may include a side port 41. In some embodiments, the first fluid pathway 56 and/or the second fluid pathway 58 may extend through the side port 41 and the primary catheter 48. In some embodiments, the second fluid pathway 58 may extend through the secondary catheter 12, and the first fluid pathway 56 may not extend through the secondary catheter 12. In some embodiments, at least a portion of the first fluid pathway 56 may be disposed in a gap between the secondary catheter 12 and the primary catheter 48. In some embodiments, the gap may be annular.

In some embodiments, the second fluid pathway 58 may be smooth and may not include any catches for the secondary catheter 12 as it moves distally in response to activation of the fluid delivery device. In some embodiments, a first fluid may be delivered to the vasculature of the patient via the first fluid pathway 56, and a second fluid may be delivered to the vasculature of the patient via the second fluid pathway 58. In some embodiments, the first fluid may be delivered to the vasculature of the patient via the first fluid pathway 56 at a same time as the second fluid is delivered to the vasculature of the patient via the second fluid pathway 58.

In some embodiments, a medicament may be delivered to the vasculature of the patient via the first fluid pathway 56 and a flush or saline solution may be delivered to the vasculature of the patient via second fluid pathway 58. In some embodiments, the medicament may be delivered to the vasculature of the patient via the second fluid pathway 58 and the flush or saline solution may be delivered to the vasculature of the patient via the first fluid pathway 56. In these and other embodiments, extension of the secondary catheter 12 beyond the primary catheter 48 and further from an insertion site of the catheter assembly 38 may facilitate delivery of the medicament to a healthier part of the vasculature with more blood flow, which may be particularly useful when the medicament is harsh.

In some embodiments, a length of the secondary catheter 12 may vary. In some embodiments, the secondary catheter distal end 22 may be disposed distal to the primary catheter distal end 50 when the secondary catheter 12 is in the advanced position. In some embodiments, the secondary catheter 12 disposed in the advanced position may convert the catheter assembly 38 from a peripheral intravenous catheter assembly to a midline catheter assembly. In some embodiments, the secondary catheter distal end 22 may be disposed about 3 inches or more distal to the catheter adapter distal end 42. In some embodiments, the secondary catheter distal end 22 may be disposed between about 2 and about 4 inches distal to the catheter adapter distal end 42 and/or between about 0 and about 3 inches distal to the primary catheter distal end 50.

In some embodiments, a diameter of the expanded portion 32 may be greater than a diameter of a portion of the catheter system 36, which may include the catheter delivery device 10. In some embodiments, the portion of the catheter system 36 may contact the expanded portion 32 when the secondary catheter 12 is disposed in the advanced position and may act as a stop to prevent distal movement of the secondary catheter 12. In some embodiments, the portion of the catheter system 36 may be disposed anywhere within the catheter system 36, such as for example, in an extension set, a connector, a needleless connector 59, the catheter adapter 40, or the primary catheter 48.

As illustrated, for example, in FIG. 3A, in some embodiments, the fluid delivery device 60 may be coupled to the housing 14. In some embodiments, the fluid delivery device 60 may be activated, as illustrated, for example, in FIG. 3B. In some embodiments, in response to activating the fluid delivery device 60, fluid may flow distally through the housing 14 and the catheter assembly 38. In some embodiments, the fluid may advance the secondary catheter 12 through the catheter assembly 38 in a distal direction. In some embodiments, the activating the fluid delivery device 60 may provide flushing of the catheter assembly 38 and/or the vasculature as the secondary catheter 12 advanced. In some embodiments, the fluid delivery device 60 may include a syringe or another suitable fluid delivery device, which may be pre-filled with fluid.

In some embodiments, the housing 14 may be primed prior to activation of the fluid delivery device 60. In some embodiments, the housing 14 may be primed prior to coupling of the catheter delivery device 10 to the catheter assembly 38.

In some embodiments, the fluid delivery device 60 may be uncoupled from the housing proximal end 18 in response to the fluid delivery device 60 being activated and the secondary catheter 12 being moved to the advanced position. In some embodiments, a blood collection device 63, illustrated, for example, in FIG. 3C, may be coupled to the housing proximal end 18 after the fluid delivery device 60 is uncoupled from the housing proximal end 18, and a blood sample may bay be collected within the blood collection device through the secondary catheter 12. In some embodiments, the blood collection device 63 may include a vacuum tube, a test tube, a syringe, or any other suitable blood collection device.

In some embodiments, the blood collection device 63 may be uncoupled from the housing proximal end 18 and another blood collection device, which may be similar to or different from the blood collection device 63, may be coupled to the housing proximal end 18. In some embodiments, another blood sample may be collected within the other blood collection device through the secondary catheter 12. Thus, in some embodiments, multiple blood samples may be collected from the patient without withdrawing the secondary catheter 12 from the vasculature of the patient. In some embodiments, the catheter delivery device 10 may facilitate long-term placement of the secondary catheter 12. In some embodiments, the secondary catheter 12 may remain positioned within the primary catheter 48 after collecting a blood sample via the secondary catheter 12. In some embodiments, the secondary catheter 12 may remain positioned within the primary catheter 48 until the primary catheter 38 is removed due to vascular access no longer being required for the patient.

Figure 4:
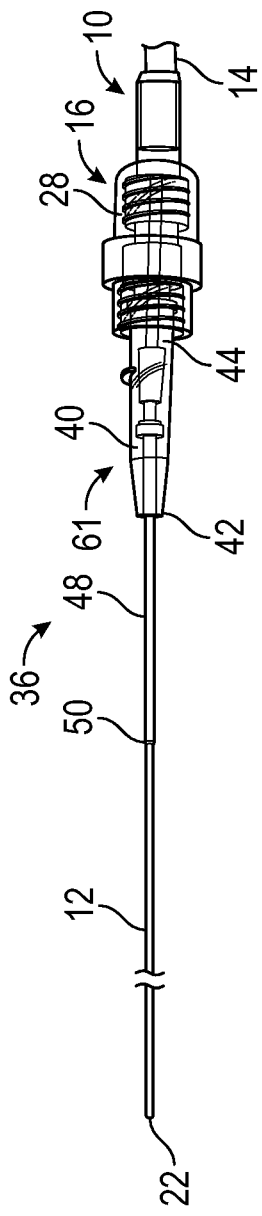
FIG. 4 is an upper perspective view of the catheter system of FIG. 3A, illustrating the catheter delivery device of FIG. 1A coupled to another example catheter assembly and illustrating the secondary catheter in the advanced position, according to some embodiments.

In some embodiments, the catheter delivery device 10 may be used with any suitable catheter assembly. Referring now to FIG. 4, in some embodiments, the catheter delivery device 10 may be coupled to a catheter assembly 61, which may be non-integrated without an extension tube extending from a side port. In these and other embodiments, the catheter system 36 may include a single fluid pathway, which may extend through the secondary catheter 12. In some embodiments, the housing distal end 16 may be coupled to the catheter adapter proximal end 44.

Figure 5:
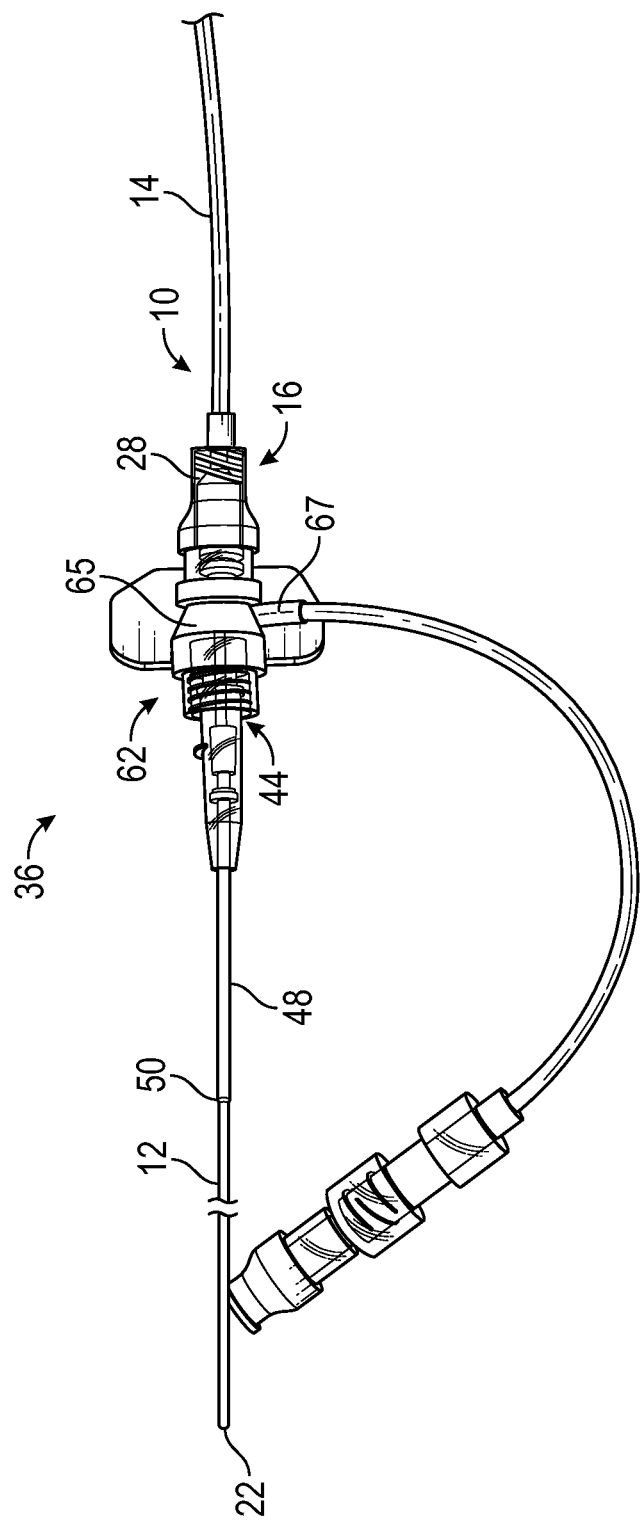
FIG. 5 is an upper perspective view of the catheter system of FIG. 3A, illustrating the catheter delivery device of FIG. 1A coupled to another example catheter assembly and illustrating the secondary catheter in the advanced position, according to some embodiments.

Referring now to FIG. 5, in some embodiments, the catheter delivery device 10 may be coupled to a catheter assembly 62, which may include a T-connector 65 coupled to the catheter adapter proximal end 44. In some embodiments, the catheter assembly 62 may include the first fluid pathway 56 and the second fluid pathway 58. In some embodiments, the first fluid pathway 56 may be separate from and not in fluid communication with the second fluid pathway 58 within the catheter assembly 62.

In some embodiments, the catheter delivery device 10 may be coupled to a first port of the T-connector 65, which may be aligned with a longitudinal axis of the primary catheter 48. In some embodiments, the first fluid pathway 56 may extend through another port 67 of the T-connector 65 and between the primary catheter 48 and the secondary catheter 12. In some embodiments, the second fluid pathway 58 may extend through the secondary catheter 12.

Figure 6A:
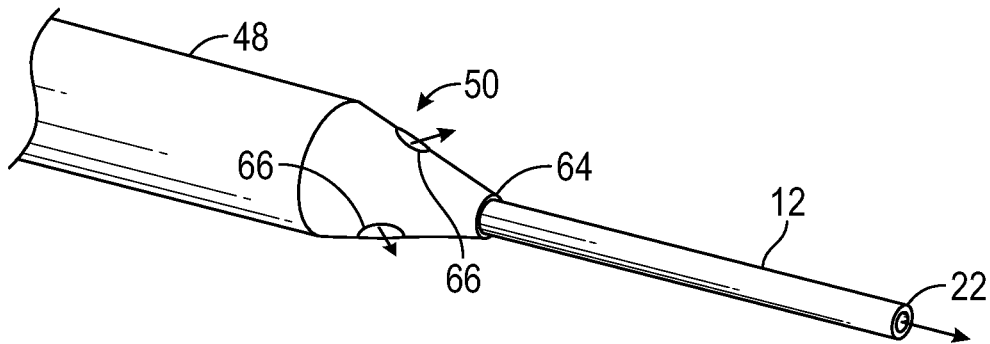
FIG. 6A is an upper perspective view of an example distal end of the catheter system of FIG. 3A, illustrating an example primary catheter having one or more diffuser holes and the secondary catheter, according to some embodiments.
Figure 6B:
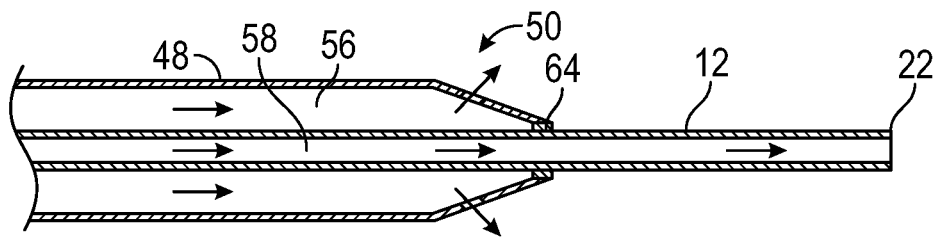
FIG. 6B is a cross-sectional view of the distal end of FIG. 6A, according to some embodiments.

Referring now to FIGS. 6A-6B, in some embodiments, the primary catheter distal end 50 may include a distal opening 64. In some embodiments, the primary catheter distal end 50 may include one or more diffuser holes 66, which may be bored through the primary catheter distal end 50. In some embodiments, the diffuser holes 66 may be angled. In some embodiments, the distal opening 64 may contact all or a portion of an outer circumference of the secondary catheter 12. In some embodiments, the diffuser holes 66 may allow fluid to exit the first fluid pathway 56 into the vasculature of the patient. In some embodiments, the diffuser holes 66 may be positioned at the primary catheter distal end 50 and/or anywhere along the primary catheter 48.

Figure 7A:
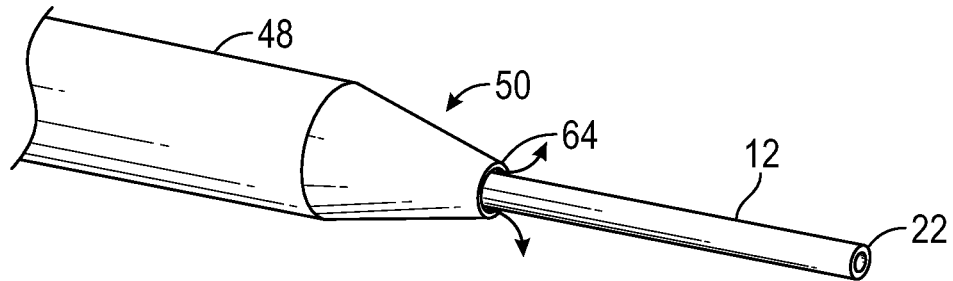
FIG. 7A is an upper perspective view of another example distal end of the catheter system of FIG. 3A, illustrating the secondary catheter having a smaller diameter than a distal opening of the primary catheter, according to some embodiments.
Figure 7B:
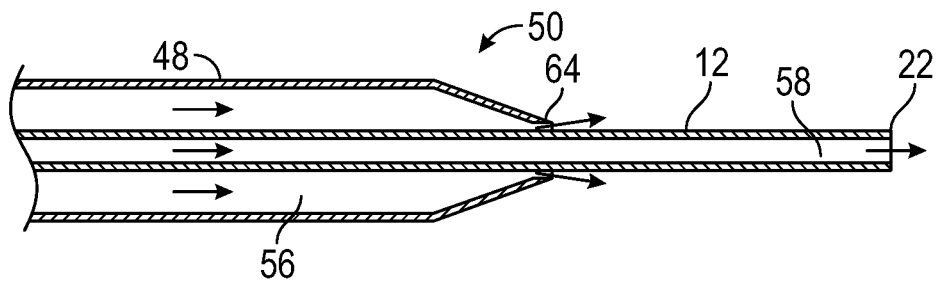
FIG. 7B is a cross-sectional view of the distal end of FIG. 7A, according to some embodiments.

Referring now to FIGS. 7A-7B, in some embodiments, an outer circumference of the secondary catheter 12 may be spaced apart from the distal opening 64 of the primary catheter distal end 50 such that fluid in the first fluid pathway 56 may flow distally between the distal opening 64 and the secondary catheter 12.

Figure 8A:
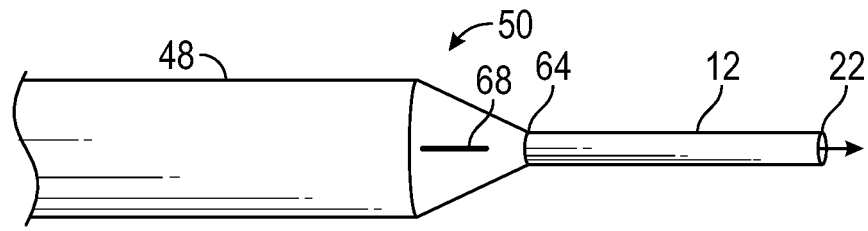
FIG. 8A is an upper perspective view of another example distal end of the catheter system of FIG. 3A, illustrating an example slit in a closed position, according to some embodiments.
Figure 8B:
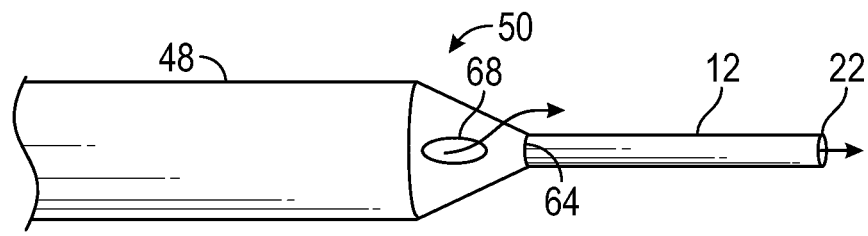
FIG. 8B is a cross-sectional view of the distal end of FIG. 8A, illustrating the slit in an open position, according to some embodiments.

Referring now to FIGS. 8A-8B, in some embodiments, the distal opening 64 of the primary catheter distal end 50 may contact the outer circumference of the secondary catheter 12. In some embodiments, the primary catheter distal end 50 may be closed and may include a slit 68, which may be configured to be closed under normal physiological pressures. In some embodiments, in response to a predetermined pressure differential, the slit 68 may open. In some embodiments, the slit 68 may open during infusion of fluid into the patient via the primary catheter 48. In some embodiments, the slit 68 may be positioned at the primary catheter distal end 50 and/or anywhere along the primary catheter 48.

In some embodiments, all or a portion of the primary catheter 48 may be constructed of silicon. In some embodiments, a portion of the primary catheter 48 that includes the slit 68 may be constructed of silicon. In some embodiments, all or a portion of the primary catheter 48 may be constructed of polyurethane or another suitable plastic. In some embodiments, the portion of the primary catheter 48 that includes the slit 68 may be constructed of polyurethane or another suitable plastic.

In some embodiments, the slit 68 may include a longitudinal slit oriented along a longitudinal axis of the primary catheter 48. In some embodiments, when the slit 68 is in the closed position, opposing faces of the slit 68 may contact each other. In some embodiments, the slit 68 may be in the closed position and sealed under normal physiological pressures, preventing fluid from flowing through the slit 68. In some embodiments, the primary catheter 48 may be resistant to occlusion and thrombosis because the slit 68 may be closed under normal physiological pressures, preventing blood from diffusing into the primary catheter 48.

Figure 9A:
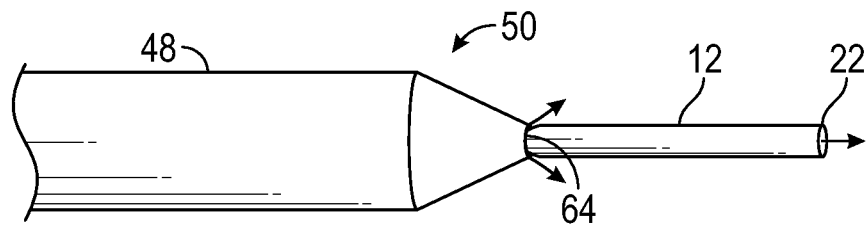
FIG. 9A is an upper perspective view of another example distal end of the catheter system of FIG. 3A, illustrating the secondary catheter flexed in response to fluid infusion, according to some embodiments.
Figure 9B:
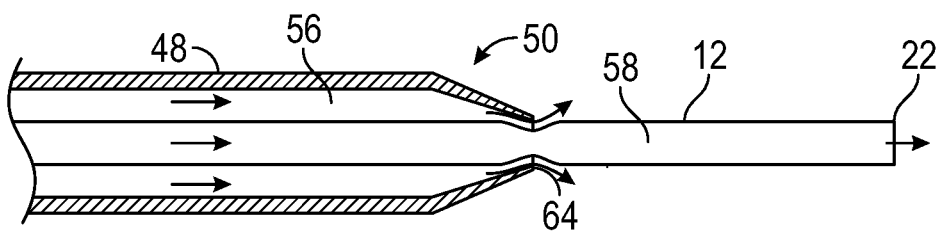
FIG. 9B is a cross-sectional view of the distal end of FIG. 9A, according to some embodiments.

Referring now to FIGS. 9A-9B, in some embodiments, the secondary catheter 12 may flex or collapse in response to a fluid pressure from fluid flowing in a distal direction through the primary catheter 48 between the outer surface of the secondary catheter 12 and the inner surface of the primary catheter 48. In some embodiments, flexing or collapsing of the secondary catheter 12 may result in infusion of fluid into the patient through the first fluid pathway 56. In some embodiments, the other fluid delivery device (not illustrated) may be coupled to the catheter adapter 40 and activated to cause the fluid pressure flowing in the distal direction through the primary catheter 48.

Figure 10A:
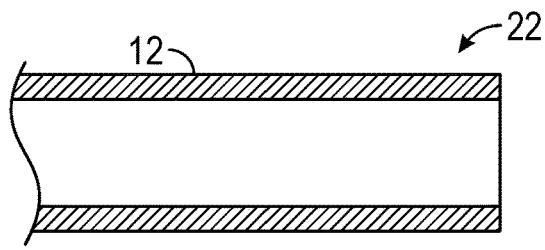
FIG. 10A is a cross-sectional view of an example distal end of the secondary catheter of the catheter delivery device of FIG. 1A, according to some embodiments.
Figure 10B:
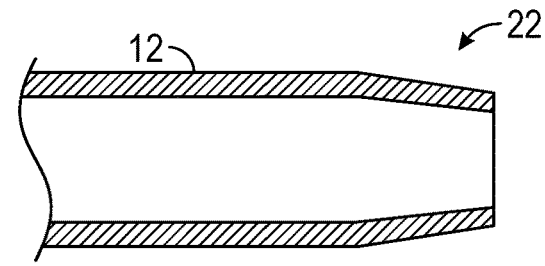
FIG. 10B is a cross-sectional view of another example distal end of the secondary catheter of the catheter delivery device of FIG. 1A, according to some embodiments.

In some embodiments, the secondary catheter distal end 22 may include any suitable tip. Referring now to FIG. 10A, in some embodiments, the secondary catheter distal end 22 may include a blunt tip, which may correspond to a standard tip. Referring now to FIG. 10B, in some embodiments, the secondary catheter distal end 22 may include a tapered, curved, rounded, or chamfered tip.

Figure 10C:
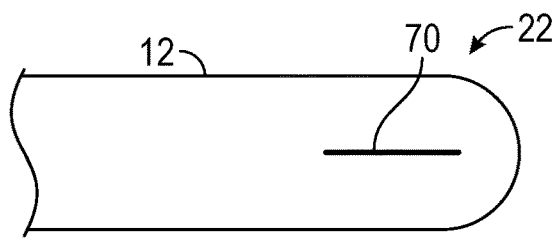
FIG. 10C is a cross-sectional view of another example distal end of the secondary catheter of the catheter delivery device of FIG. 1A, according to some embodiments.

Referring now to FIG. 10C, in some embodiments, the secondary catheter distal end 22 may be closed and may include a slit 70 configured to be closed under normal physiological conditions. In some embodiments, the slit 70 may include or correspond to the slit 68 discussed with respect to FIGS. 8A-8B. In some embodiments, in response to a predetermined pressure differential, the slit 70 may open. In some embodiments, the slit 70 may open during infusion of fluid into the patient via the secondary catheter 12. In some embodiments, the slit 70 may open during withdrawal of blood from the patient via the secondary catheter 12.

In some embodiments, all or a portion of the secondary catheter 12 may be constructed of silicon. In some embodiments, a portion of the secondary catheter 12 that includes the slit 70 may be constructed of silicon. In some embodiments, the portion of the secondary catheter 12 that includes the slit 70 may be constructed of polyurethane or another suitable plastic.

In some embodiments, the slit 70 may include a longitudinal slit oriented along a longitudinal axis of the secondary catheter 12. In some embodiments, when the slit 70 is in the closed position, opposing faces of the slit 70 may contact each other. In some embodiments, the slit 70 may be in the closed position and sealed under normal physiological pressures, preventing fluid from flowing through the slit 70. In some embodiments, the secondary catheter 12 may be resistant to occlusion and thrombosis because the slit 70 may be closed under normal physiological pressures, preventing blood from diffusing into the secondary catheter 12.

Figure 10D:
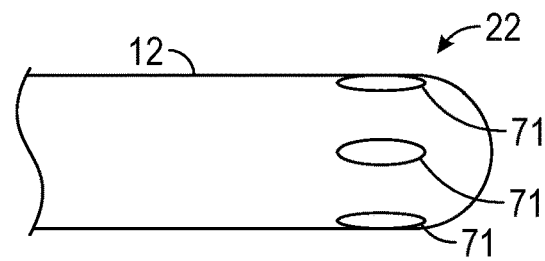
FIG. 10D is a cross-sectional view of another example distal end of the secondary catheter of the catheter delivery device of FIG. 1A, according to some embodiments.
Figure 10E:
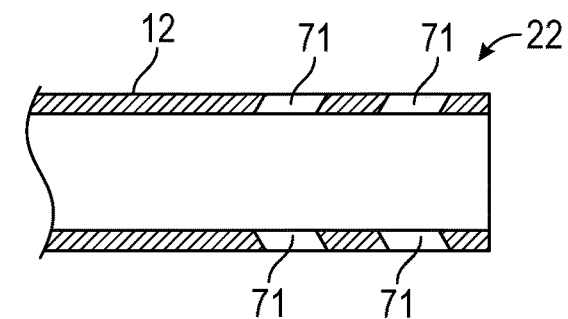
FIG. 10E is a cross-sectional view of another example distal end of the secondary catheter of the catheter delivery device of FIG. 1A, according to some embodiments.

Referring now to FIGS. 10D and 10E, in some embodiments, the secondary catheter distal end 22 may include one or more diffuser holes 71, which may be disposed in various patterns and configurations. In some embodiments, the diffuser holes 71, which may be bored through the secondary catheter distal end 22. In some embodiments, the diffuser holes 71 may be angled.

Figure 11A:
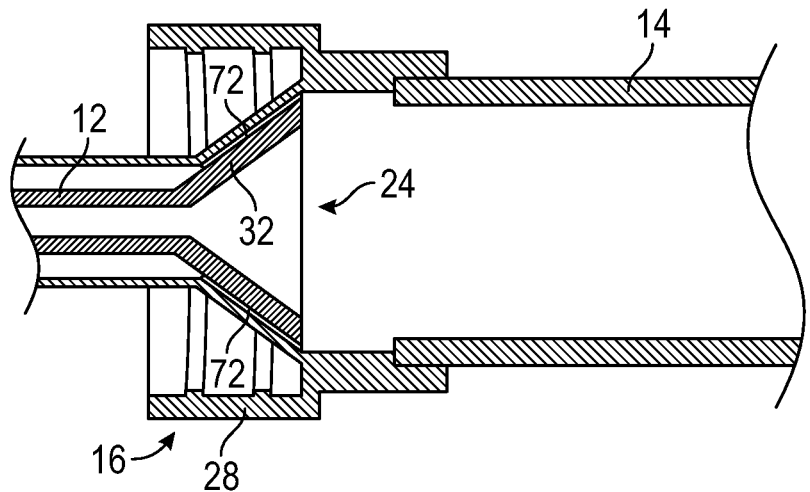
FIG. 11A is a cross-sectional view of an example expanded portion of the secondary catheter proximate example grooves of an example distal connector of the catheter delivery device of FIG. 1A, according to some embodiments.
Figure 11B:
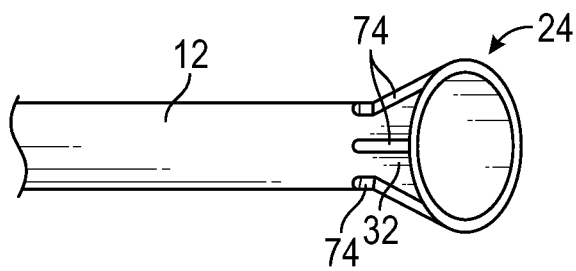
FIG. 11B is an upper perspective view of the expanded portion of FIG. 11A, illustrating example grooves disposed on the expanded portion, according to some embodiments.

Referring now to FIGS. 11A-11B, in some embodiments, in response to movement of the secondary catheter 12 to the advanced position, an outer surface of the expanded portion 32 may abut the portion of the housing lumen 20 that may act as the stop. In some embodiments, in response to the expanding portion 32 abutting the portion of the housing lumen 20 that may act as the stop, a seal may be formed, which may prevent fluid from flowing between the outer surface of the expanded portion 32 and the portion of the housing lumen 20.

In some embodiments, the portion of the housing lumen 20 may include one or more grooves 72, as illustrated, for example, in FIG. 11A. In some embodiments, the grooves 72 may be configured to allow fluid to flow from the housing proximal end 18 through the housing distal end 16, between the outer surface of the expanded portion 32 and the portion of the housing lumen 20. Additionally or alternatively, in some embodiments, as illustrated in FIG. 11B, the outer surface of the expanded portion 32 may include one or more other grooves 74, which may be configured to allow fluid to flow from the housing proximal end 18 through the housing distal end 16, between the outer surface of the expanded portion 32 and the portion of the housing lumen 20 and through the gap between the primary catheter 48 and the secondary catheter 12, which may be annular. In some embodiments, the grooves 72 and/or the other grooves 74 may facilitate flushing between the expanded portion 32 and the portion of the housing lumen 20.

Figure 12A:
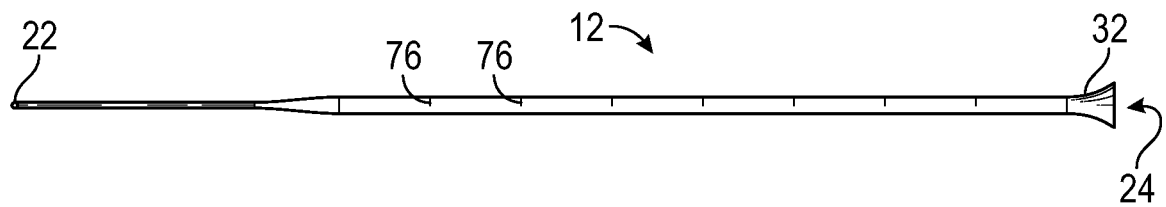
FIG. 12A is an upper perspective view of an example secondary catheter, according to some embodiments.
Figure 12B:
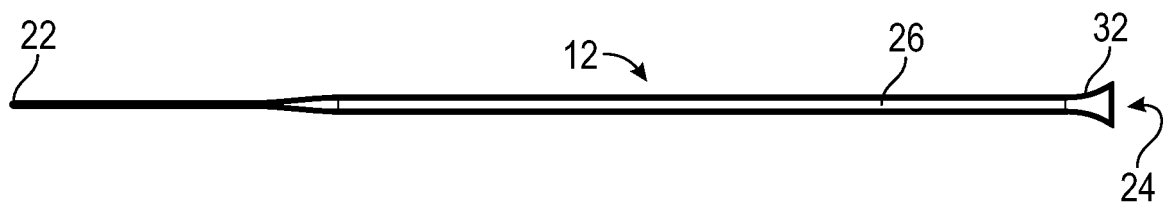
FIG. 12B is a cross-sectional view of the secondary catheter of FIG. 12A, according to some embodiments.

Referring now to FIGS. 12A-12B, in some embodiments, the secondary catheter 12 may include one or more outer diameters and/or one or more inner diameters. In some embodiments, the secondary catheter 12 may include a multi-diameter catheter, which may be described, for example, in U.S. Patent Application No. 62/660,646, filed Apr. 20, 2018, entitled "MULTI-DIAMETER CATHETER AND RELATED DEVICES AND METHODS," which is incorporated herein by reference. In these and other embodiments, the secondary catheter 12 may include the expanded portion 32 disposed at or near the secondary catheter proximal end 24. In some embodiments, the secondary catheter 12 having one or more transition portions may allow improved blood flow rates during blood collection.

In some embodiments, the secondary catheter 12 may include tubing. In some embodiments, the tubing may be co-extruded to provide various structural improvements (layers, axial stripes, etc.). In some embodiments, one or more transition portions may be constructed by extrusion of a continuous tube, which may be monolithically formed as a single unit, or by joining multiple tubes of varying inner and outer diameters together. In some embodiments, the multiple tubes may be constructed of a same or different material. In some embodiments, the multiple tubes may bonded, swaged, tipped, welded, or joined via another suitable method.

In some embodiments, the housing 14 may be transparent. In some embodiments, the secondary catheter 12 may include one or more markings 76, which may indicate to the clinician a position of the secondary catheter distal end 22 within the catheter assembly or beyond the primary catheter.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A catheter delivery device, comprising:
a housing, comprising a housing distal end, a housing proximal end, and a housing lumen extending through the housing distal end and the housing proximal end, wherein the housing distal end is configured to couple to a catheter assembly, wherein the housing proximal end is configured to couple to a fluid delivery device; and
a secondary catheter, comprising a secondary catheter distal end, a secondary catheter proximal end, and a secondary catheter lumen extending through the secondary catheter distal end and the secondary catheter proximal end, wherein the secondary catheter is disposed within the housing, wherein the secondary catheter is configured to move distally to an advanced position in response to a fluid pressure provided by the fluid delivery device, wherein the secondary catheter distal end is disposed distal to the housing distal end when the secondary catheter is in the advanced position.

2. The catheter delivery device of claim 1, wherein the housing distal end comprises a male luer adapter.

3. The catheter delivery device of claim 1, wherein the housing proximal end comprises a female luer adapter.

4. The catheter delivery device of claim 1, wherein the housing comprises an extension tube.

5. The catheter delivery device of claim 1, wherein the secondary catheter comprises an expanded portion, wherein a diameter of the expanded portion is greater than a diameter of a portion of the housing lumen, wherein the portion of the housing lumen contacts the expanded portion when the secondary catheter is disposed in the advanced position and acts as a stop to prevent distal movement of the secondary catheter.

6. The catheter delivery device of claim 5, wherein the housing comprises an extension tube, further comprising a clamp disposed on the extension tube, wherein a position of the clamp along the extension tube is adjustable, wherein in response to placement of the clamp at the portion of the housing lumen, the portion of the housing lumen contacts the expanded portion when the secondary catheter is disposed in the advanced position and acts as a stop to prevent distal movement of the secondary catheter.

7. The catheter delivery device of claim 5, wherein in response to the expanded portion contacting the portion of the lumen, a seal between the expanded portion and the portion of the lumen is formed.

8. The catheter delivery device of claim 5, wherein an outer surface of the expanded portion comprises a first plurality of grooves or the portion of the lumen comprises a second plurality of grooves, wherein the first plurality of grooves or the second plurality of grooves are configured to allow fluid to flow from the housing proximal end through the housing distal end.

9. The catheter delivery device of claim 1, wherein the housing is transparent, wherein an outer surface of the secondary catheter or an outer surface of the housing comprises a plurality of markings to indicate to a clinician a position of the secondary catheter distal end.

* * * * *